United States Patent
Verdonck et al.

[11] Patent Number: 5,905,055
[45] Date of Patent: May 18, 1999

[54] HETEROGENEOUS METATHESIS CATALYST

[75] Inventors: Ludo C. G. C. Verdonck, Nazareth; Francis W. C. Verpoort, Lichtervelde; Antoine R. J. Bossuyt, Harelbeke, all of Belgium

[73] Assignee: DSM N.V., Heerlen, Netherlands

[21] Appl. No.: 08/741,971

[22] Filed: Oct. 31, 1996

Related U.S. Application Data

[63] Continuation of application No. PCT/NL95/00159, May 2, 1995.

[30] Foreign Application Priority Data

May 3, 1994 [BE] Belgium .................... 9400449

[51] Int. Cl.[6] .......................... B01J 23/16; B01J 31/00; C07C 6/02
[52] U.S. Cl. .................... 502/311; 502/353; 502/152; 502/228; 585/646; 585/647; 585/645
[58] Field of Search .................... 502/152, 154, 502/164, 228, 311, 353, 255, 254, 241; 585/646, 647, 645

[56] References Cited

U.S. PATENT DOCUMENTS

| | | | |
|---|---|---|---|
| 3,557,199 | 1/1971 | Parthasarathy et al. | 562/535 |
| 3,647,908 | 3/1972 | Medema et al. | 585/645 |
| 3,974,231 | 8/1976 | Keupper et al. | 585/372 |
| 4,046,832 | 9/1977 | Nowak et al. | 585/645 |
| 4,415,480 | 11/1983 | Murrell et al. | 502/242 |
| 4,918,039 | 4/1990 | Martin | 502/113 |
| 4,931,561 | 6/1990 | Shizumi et al. | 544/336 |
| 5,275,994 | 1/1994 | Weissman et al. | 502/171 |

FOREIGN PATENT DOCUMENTS

| | | |
|---|---|---|
| 0 360 262 A2 | 9/1989 | European Pat. Off. . |
| 1 555 139 | 1/1969 | France . |
| 2 326 196 | 12/1974 | Germany . |
| 1193943 | 1/1969 | United Kingdom . |
| 1193943 | 6/1970 | United Kingdom . |

*Primary Examiner*—Glenn Caldarola
*Assistant Examiner*—Thuan D. Dang
*Attorney, Agent, or Firm*—Pillsbury Madison & Sutro LLP

[57] ABSTRACT

The invention relates to a heterogeneous metathesis catalyst containing a support, a metal compound chosen from the group consisting of tungsten, rhenium and molybdenum, and a promoter, the promoter consisting of a niobium compound. The catalyst according to the invention has a high activity at low temperatures. The invention also relates to a process for the metathesis of olefins.

15 Claims, No Drawings

5,905,055

HETEROGENEOUS METATHESIS CATALYST

This is a Continuation of International Appln. No. PCT/NL95/00159 filed May 2, 1995 which designated the U.S.

BACKGROUND OF THE INVENTION

1. Field of the Invention

The invention relates to a heterogeneous metathesis catalyst comprising a support, a metal compound the metal of which has been chosen from the group formed by tungsten, rhenium and molybdenum, and a promoter. The invention also relates to a catalytic process for the metathesis of olefins.

2. Description of Related Art

A metathesis is a reaction in which olefins are catalytically converted into other olefins having a different molecular weight through exchange between olefin molecules of groups situated at the double bond of the olefin molecule. An example is the conversion, through metathesis, of 2-pentene into 2-butene and 3-hexene until a reaction equilibrium is attained. In a heterogeneous metathesis catalyst a catalytically active metal compound is attached to the surface of a fixed support, so that the catalyst can readily be separated from the reaction mixture.

Besides the support and the catalytically active metal compound, known heterogeneous metathesis catalysts often contain promoters to improve the activity of the catalyst. Activity here and hereinafter is understood to be the weight of the converted olefins per unit weight of catalyst 5 minutes after the start of the reaction.

EP-A-152,112 discloses such a heterogeneous metathesis catalyst consisting of a tungsten oxide on a silica support containing a titanium-containing compound as promoter to increase the activity of the catalyst.

Drawbacks of the known heterogeneous metathesis catalyst are the low activity and the very high temperature at which the catalyst is only active (300–500° C.).

SUMMARY OF THE INVENTION

The object of the invention is to provide a heterogeneous metathesis catalyst having a higher activity.

This object is achieved according to the invention in that the promoter comprises a niobium compound.

Accordingly, the present invention is directed to a heterogeneous metathesis catalyst comprising a support, a metal compound, and a promoter. The metal compound is selected from tungsten, rhenium and molydenum and the promoter is a niobium compound. The catalyst is activated with an alkylating organometal compound.

It has been found that the heterogeneous metathesis catalyst according to the invention (hereafter to be referred to as "catalyst according to the invention") has a very high activity. Another advantage of the catalyst according to the invention is an unexpected good activity at room temperature. It has further been found that the catalyst according to the invention is very suitable for ring opening metathesis polymerization and for acyclic diene metathesis.

Tanabe (in Catalysis Today, 8 (1990), 1–11) describes the use of niobium and niobium compounds as catalyst or as component of a catalyst for various reactions. However, it is not stated that niobium can be active as a promoter in metathesis reactions. In particular, it is not stated that a niobium compound can be used in combination with a support and a catalytic metal compound the metal of which is chosen from the group formed by tungsten, rhenium and molybdenum.

J. Chem. Soc., Chem. Comm. (1993), 361—361, describes a metathesis catalyst of which the support consists entirely of niobium oxide ($Nb_2O_5$) onto which a tungsten alkylidene compound has been applied. Compared with the catalyst according to the invention this metathesis catalyst has a low activity.

DETAILED DESCRIPTION OF THE PREFERRED EMBODIMENT

In the catalyst according to the invention the niobium compound can be attached in various ways. The niobium compound can for instance be attached to a catalyst with the metal compound attached directly to the support.

Most preferably, the surface of the support in the catalyst according to the invention is modified in that a layer of the metal compound wholly or partly covers a modified support, comprising the support wholly or partly covered with a layer of the niobium compound. Preferably, the layer of the niobium compound is a niobic acid monolayer. In this embodiment the catalyst according to the invention has an extremely high activity. A monolayer is here and hereinafter understood to be a layer having a thickness approximately equal to the size of one molecule.

In itself a catalyst is known from Catalysis Today, 8 (1990), 57–66 (Shirai et al.), which consists of silica covered with a niobium compound. It is stated that this catalyst can be used as a catalyst for dehydrogenation, dehydration and esterification of ethanol. It is not stated that this catalyst, in combination with a metal compound the metal of which is chosen from the group consisting of tungsten, rhenium and molybdenum, can be used as a heterogeneous metathesis catalyst.

The support in the catalyst according to the invention is a solid with a large specific surface. The specific surface of the support is preferably at least 50 $m^2/g$. For a high activity the specific surface is preferably larger than 150 $m^2/g$ and more preferably larger than 300 $m^2/g$. Preferably an oxide is used as support. Suitable supports consist of one or more of the support materials chosen from the group consisting of silica, alumina, magnesia, titania, zirconia or mixed oxides of these. Most preferably the support consists substantially of silica. The surface of such a silica support preferably has a content of hydroxyl groups of 2–5 $OH/nm^2$. More preferably the content of hydroxyl groups at the surface is higher than 3, and even more preferably higher than 4.5 $OH/nm^2$. This has the advantage that the catalyst according to the invention has a higher activity. In particular this makes it possible to realize a high coverage of the niobium compound layer on the surface of the support.

Preferably the layer of the metal compound is a monolayer which preferably fully covers the surface of the support, which may be modified with a niobium compound or not. This results in a higher activity of the catalyst according to the invention. The amount of metal compound in the catalyst is preferably 1 to 10 wt. %, more preferably 3 to 8 wt. %, and most preferably 4 to 8 wt. % (relative to the total weight of the support, the niobium compound and the metal compound).

In the catalyst according to the invention the metal in the metal compound is preferably tungsten. It has been found that the advantages of the invention are more pronounced if tungsten is used.

Various compounds are suitable for use as the metal compound in the catalyst. Good results are achieved with metal oxides, metal halogenides and organometallic complexes of tungsten, rhenium and molybdenum. The metal compound preferably contains one or more organic ligands such as alkyl, aryl, alkoxy, aryloxy, carbonyl, alkylidene or π-bonded hydrocarbons. It has been found that a catalyst according to the invention in which the metal compound contains one or more organic ligands has a high activity at a lower temperature.

In the catalyst according to the invention a metal complex is attached to the modified support by oxygen bridges, the metal complex being of the formula:

$$M(X)_n(R)_m(O)_p \tag{1}$$

where:

M: tungsten, rhenium, molybdum

X : halogen, OH

R : organic groups, different or the same, chosen from the group consisting of alkyl, aryl, alkoxy, aryloxy, carbonyl, alkylidene or π-bonded hydrocarbons, containing 1–25 carbon atoms;

O: oxygen bridge to the support n+m+p=5, 6 or 7 p=1, 2 or 3.

Depending on the nature of the groups bound to the metal and on the reaction conditions, in the catalyst that can be obtained by means of the above-mentioned reaction, 1 to 3 (usually 2) of the X- or R-groups may have been split off and replaced by a bond with the support. In addition, further X- or R-groups may have been split off.

Any halogen ligands still present in the catalyst as obtainable by the above-mentioned reaction are preferably replaced by oxyligands, being hydroxyl or double bonded oxygen ligands. This can simply be effected by exposing the catalyst to humid air. A catalyst with such oxyligands has a higher activity.

Examples of π-bonded hydrocarbons are π-bonded alkenes, aromatic rings or ionogenic cyclic alkenes having an aromatic character. Good results are achieved if the organometallic complex contains one or more π-bonded allyl or cyclopentadienyl groups, such as the cyclopentadienyl complex π—C_5H_5W(CO)_3Cl.

The organometallic complex preferably contains one to four substituted or non-substituted aryloxy groups. Most preferably two aryloxy groups are present. It has been found that these aryloxy groups remain bonded to the metal during the reaction with the modified support and have a favourable effect on the activity and selectivity of the catalyst. A further advantage is that this catalyst is very suitable for ring opening metathesis polymerization and for acyclic diene metathesis. The R-groups are preferably 2,6-disubstituted phenoxy groups. The substituents are preferably halogens or alkyl groups.

It has further been found that the stability and selectivity of the catalyst according to the invention are improved if the R-group in formula 1 contains 12 or more carbon atoms. This is the case in particular if R is a bidentate ligand. A bidentate ligand is understood to mean an organic group which can be bonded to a catalytically active metal at two sites. Preferably a substituted diphenyldioxy group is used for this, such as 5,5'-dimethoxy-3,3'-di-t-butyl-2,2'-biphenyldioxy (MBPD).

A high activity at low temperatures is obtained with a catalyst according to the invention which is activated with an alkylating organometallic compound (hereinafter called activator). This results in high activity at low temperatures, which reduces the risk of any temperature-sensitive organic ligands present being split off from the catalytically active metal compound. Without being bound to any scientific theory it is assumed that the activator creates a carbene complex on the metal compound.

Good results are achieved with an aluminium alkyl compound or a Grignard compound as activator. Most preferably the activator is an isobutyl aluminium dihalide.

A further advantage of the use of an alkoxy- or aryloxy group in the metal compound is that the catalyst system, if activated before the metathesis reaction, remains longer active with the same amount of activator, while in addition the activity of the catalyst system is not affected, or less so, by an activator excess.

In a special embodiment of the invention the metal compound is a metal carbene complex. This has the advantage that the catalyst in itself already has a good activity at a low temperature without activation with an alkylating organometallic compound.

The catalyst according to the invention may optionally contain other components as well. The catalyst may for instance contain co-components for further improvement of the activity or for purposes other than catalysis of the metathesis reaction. An example of another purpose is isomerization of olefins obtained during the metathesis reaction (for instance with MgO or V_2O_5).

The embodiment of the catalyst according to the invention that is most preferred, the best mode, contains a silica support which is modified with a niobic acid monolayer covering all or part of the surface of the support and a tungsten compound covering all or part of the surface of the modified support which preferably contains aryloxy or alkoxy ligands and which has been activated with an aluminium alkyl compound.

It has further been found that a catalyst containing a silica support which is covered wholly or partly with a monolayer of a tungsten compound which contains one or more organic ligands, preferably aryloxy or alkoxy ligands, and which has been activated with an aluminium alkyl compound, has a higher metathesis activity even at low temperatures in comparison with the catalysts known so far. It has further been found that this catalyst is suitable for the metathesis of functionalized olefins, Preferred embodiments and associated advantages of the catalyst according to the invention apply likewise to this catalyst. Functionalized olefins are olefins that contain one or more groups with heteroatoms, such as unsaturated carboxylic acids, carboxylic acid esters, alcohols, nitriles or halogens.

The invention also relates to a process for the preparation of a catalyst according to the invention. The catalyst according to the invention can be prepared in various ways. It can for instance be prepared by attaching a niobium compound as promoter to a precursor consisting of the (catalytically active) metal compound on a support. This can be effected using various ways known in themselves, for instance by chemical reaction of the precursor with a niobium compound or by precipitating a niobium compound from a solution onto the precursor, by soaking in or spraying with a solution followed by drying or heating. Preferably the catalyst according to the invention is prepared by attaching a niobium compound to a support and then attaching the metal compound to the modified support. Suitable methods for attaching a niobium compound, in particular a niobic acid monolayer, to a support are described in the above-mentioned publication by Shirai et al.

Most preferably the heterogeneous metathesis catalyst according to the invention is prepared using a process comprising the following steps:

(a) reacting, in a solvent and in the absence of water and oxygen, a support with a niobium compound;

(b) treatment of the reaction product obtained in (a) with a solution of an ammonium salt or ammonium hydroxide, (c) heating the reaction product obtained in (b) at a temperature between 100 and 300° C. at reduced pressure;

(d) moistening the reaction product obtained in (c) with water;

(e) heating the reaction product obtained in (d) at a temperature between 100 and 300° C. at reduced pressure;

(f) attaching the metal compound to the modified support obtained in (e). The niobium compound preferably is $Nb(O-R^1)_5$ with each $R^1$ being an alkyl, aryl, alkaryl, aralkyl group or mixtures of these groups, $R^1$ generally containing 1–20 carbon atoms.

In steps (a) through (e) a niobic acid monolayer is formed. The support, preferably silica, is preferably heated at a temperature between 100 and 300° C. before reaction step (a) so as to obtain a high content of hydroxyl groups on the surface and remove the physically adsorbed water.

The solvent mentioned under (a) is a solvent that is inert for the reaction, for instance n-hexane. If the niobium compound in step (a) is $Nb(O-R^1)_5$, the $O-R^1$ group is preferably an ethoxide. Between step (a) and step (b) the reaction product obtained in step (a) is preferably heated at a temperature between 100 and 300° C. and at reduced pressure in order to promote and complete the attaching reaction.

The metal compound used in step (f) preferably is of the formula

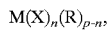

$$M(X)_n(R)_{p-n},$$

where:

M : W, Re, Mo

X : halogen

R : groups, different or the same, chosen from the group formed by alkyl, aryl, alkoxy, aryloxy, carbonyl, alkylidene or π-bound hydrocarbons, generally containing 1–25 carbon atoms;

n=1 to (p-1), p=5, 6 or 7.

Attaching of the catalytically active metal compound to the modified support (step f) can be effected in ways that are known for support materials such as silica and alumina. The catalytically active metal compound is preferably attached through chemisorption on the modified support of a compound of the metal, such as a metal halogenide or an organometallic compound. This generally results in the formation of a monolayer of the catalytically active metal compound on the modified support. It has been found that such catalysts are more active. The reaction of the metal compound with the modified support can be effected by contacting the support, in the absence of water and oxygen, in a solvent with the organometallic complex and refluxing the reaction mixture. The solvent is preferably an inert solvent boiling at a low temperature, such as n-hexane.

Catalyst activation preferably takes place shortly before the catalyst is contacted with the olefins. During catalyst activation the catalyst according to the invention is reacted with an alkylating organo-metallic compound. The amount of activator is preferably larger than 0.01 mmol and preferably smaller than 2 mmol per 100 mg of catalyst. Preferably the amount is smaller than 1, and most preferably smaller than 0.5 mmol per 100 mg of catalyst. The molar ratio between activator and amount of catalytically active metal in the metal compound is preferably higher than 1 and preferably lower than 200, more preferably lower than 100, and most preferably lower than 75. It has been found that too large an amount of activator may have a negative effect on the activity of the catalyst. One skilled in the art will simply be able to determine the optimum amount.

If the activity of the catalyst according to the invention has decreased during the metathesis reaction, this activity can again be increased by means of another activator addition to the catalyst.

With the heterogeneous metathesis catalyst according to the invention very fast and very high metathesis conversion with a good selectivity can be achieved at a low temperature. The invention therefore also relates to a process for the metathesis of olefins in which use is made of a heterogeneous metathesis catalyst according to the invention, or as obtainable through the the process described above for the preparation of such catalyst. The temperature at which the metathesis reaction is carried out is preferably between −20 and +100° C., more preferably below 50° C. and most preferably the process is carried out at a temperature between 0 and 30° C. The advantage of a low metathesis reaction temperature is on the one hand that process operation is economically more attractive for energy reasons and on the other hand that the metathesis reaction is more selective (e.g. less isomerisation occurs). Although the advantages of the invention are manifest in particular at a low temperature, very good results are obtained also at high temperatures, for instance in a gas phase process.

The invention will below be illustrated on the basis of examples and comparative experiments. To test the catalysts the conversion was measured as a function of time in the metathesis of 2-pentene (2-P) to 2-butene (2-B) and 3-hexene (3-H). Unless stated otherwise, all activities described below were performed in an argon atmosphere (atmospheric pressure) with exclusion of air.

EXAMPLES

Measurement Of Conversion

At various points during the metathesis reaction samples were taken of the gas above the reaction mixture. The sample was analyzed using gas chromatographic mass spectrometry (GC-MC: Varian Finnigan-Matt). The concentrations of the components were calculated from the GC peak areas via a response factor predetermined for each component. The conversion was calculated as the fraction (in mol. %) of the sum of the reaction products (for 2-pentene (2-P): 2-butene (2-B) plus 3-hexene (3-H)). For metathese reactions of this type the degree of conversion at the reaction equilibrium is generally around 50%. However, since the gas phase, owing to the higher volatility of 2-B, is richer in 2-B than the liquid phase, degrees of conversion in excess of 50% are found.

Preparation Of A Modified Support: Niobic Acid Monolayer On Silica 1.1128 g $NbCl_5$ and 30 ml n-hexane were introduced into a 100 ml three-neck flask. With constant stirring 1.202 ml EtOH was added to the suspension. The suspension was subsequently refluxed for one hour. A clear solution of the $Nb(OEt)_5$ was obtained. The niobic acid monolayer on silica $(SiO_2)$ was prepared using this $Nb(OEt)_5$. 6 g Silica (Polypor$^R$, specific surface: 345 m$^2$/g) was preheated at 200° C. for 2 hours to obtain an OH concentration of about 5

OH/nm$^2$ (determined by infrared analysis according to Anal. Chem. 1989, 61, 41–47). The hexane solution of Nb(OEt)$_5$ was subsequently transferred to the silica. The flask that had contained the Nb(OEt)$_5$ was rinsed with 40 ml dry hexane, following which the hexane was added to the silica. After refluxing and settling of the reaction product the supernatant liquid was removed and the reaction product was subsequently washed three times with n-hexane. Subsequently the reaction product was heated at 200° C. under vacuum for 1 hour to promote the attaching reaction. The treated silica was then treated with a 1M NH$_4$OH solution to convert the Nb—OC$_2$H$_5$ units into Nb—O$^-$NH$_4^+$ units. After one hour's gentle stirring the supernatant solution was removed. The ammonium cations obtained were subsequently decomposed at 200° C. under vacuum for one hour. The Nb-modified silica was then treated with about 5 ml H$_2$O and heated at 200° C. under vacuum for 2 hours, which yielded the niobic acid monolayer.

Comparative Experiment A:

SiO$_2$/WCl$_4$(—O—2. 6—C$_6$H$_3$Br$_2$)$_2$/iBAC 1.45 g WCl$_6$ and 30 mm CCl$_4$ were introduced into a flask, following which a solution of 1.8473 g C$_6$H$_3$Br$_2$OH in 30 ml CCl$_4$ was added dropwise in a period of 15 minutes. During Cl substitution by the phenol derivative, the colour of the solution turned dark red. The reaction mixture was refluxed for 3 hours, after which the solvent was removed at reduced pressure and at 80° C. Five grams of silica, previously calcined at 300° C. for 6 hours, was heated at 120° C. at reduced pressure in order to remove physically adsorbed water. A solution of 0.5 g of the above-mentioned WCl$_4$(—O—2.6—C$_6$H$_3$Br$_2$)$_2$ in 40 ml CCl$_4$ was transferred to the pretreated silica. The reaction mixture was refluxed for 4 hours while being stirred thoroughly. The resulting catalyst was then filtered and washed with CCl$_4$.

Measurement Of The Conversion 100 mg Catalyst was transferred in air to the reactor and was dried for 2 hours at reduced pressure at 110–120° C. to remove the physically adsorbed water. The other activities were performed in an Ar atmosphere. After cooling, 9.65 ml chloro benzene (PhCl) and 0.1 ml isobutylaluminium dichloride (iBAC) (2.78 M) were subsequently introduced into the reactor, following which 0.25 ml 2-P was added after a 10-minute activation period. The reaction was carried out at room temperature. The conversion measured as a function of time is presented in Table 1. The catalyst was found to be active also for metathesis of methyl oleate.

TABLE 1

Conversion of 2-P as a function of time when using SiO$_2$/WCl$_4$(—O-2.6-C$_6$H$_3$Br$_2$)$_2$/iBAC as catalyst

| Time (min) | Conversion (%) |
| --- | --- |
| 5 | 50 |
| 10 | 67 |
| 20 | 82 |
| 40 | 83 |
| 60 | 83 |
| 180 | 84 |

Example I

SiO$_2$/Nb$_2$O$_5$/WCl$_4$(—O—2. 6—C$_6$H$_3$Br$_2$)$_2$/iBAC 0.5 g Of the modified support (SiO$_2$/Nb$_2$O$_5$) prepared by the method described above was heated for 2 hours at 200° C. under vacuum. A hexane solution of WCl$_4$(—O—2.6—C$_6$H$_3$Br$_2$)$_2$, prepared by the method described in comparative experiment A, was added to the modified support. The suspension was subsequently refluxed for 2 hours. The SiO$_2$/Nb$_2$O$_5$ surface assumed a dark red colour. After settling of the reaction product the supernatant liquid was removed and the reaction product was subsequently washed three times with n-hexane and dried at 120° C. under vacuum. Gravimetric analysis proved that the catalyst contains about 5 wt. % tungsten.

Measurement Of The Conversion 100 mg of the dried catalyst was transferred to the reactor vessel in an Ar atmosphere. 9.4 ml PhCl and 0.1 ml iBAC (2.78 M) were added, following which, after a 10-minute activation period, 0.5 ml 2-P was added. The reaction was carried out at room temperature. The conversion measured as a function of time is presented in Table 2.

TABLE 2

Conversion of 2-P as a function of time when using SiO$_2$/Nb$_2$O/WCl$_4$(—O-2.6-C$_6$H$_3$Br$_2$)$_2$/iBAC as catalyst

| Time (min) | Conversion (%) |
| --- | --- |
| 5 | 61 |
| 10 | 75 |
| 20 | 82 |
| 40 | 84 |
| 60 | 83 |
| 240 | 86 |

Example I proves that after 5 minutes the catalyst according to the invention, even at double the amount of 2-P, has a higher conversion and thus a significantly higher activity than the catalyst of comparative experiment A.

Comparative Experiment B

SiO$_2$/WCl$_4$(—O—2.6—C$_6$H$_3$(t-Bu)$_2$)$_2$/iBAC

A solution of 2,6-di-t-butylphenol (HO—2,6—C$_6$H$_3$(t-Bu)$_2$) (0.2328 g; 1.13.10$^{-3}$ mol) in n-hexane was added dropwise to 0.225 g WCl$_6$ in 30 ml hexane in a period of 15 minutes. During Cl substitution by the phenoxide, the colour of the solution changed into dark purple. The reaction mixture was stirred for 2 hours, after which the solvent was removed at reduced pressure. 2 g of silica was dried for 2 hours in an Ar atmosphere at 200° C. A solution of WCl$_4$ (—O—2.6—C$_6$H$_3$(t-Bu)$_2$)$_2$ was added to the pretreated silica, after which the suspension was refluxed for 2 hours. The silica turned reddish brown, while the solution lost its colour. After settling of the reaction product the supernatant liquid was removed. The reaction product was subsequently washed 3 times with n-hexane and subsequently dried at 120° C. under vacuum. The catalyst contained 5.2 wt. % tungsten.

Measurement Of The Conversion 100 mg of the catalyst was transferred to the reactor in an argon atmosphere. 9.65 ml PhCl and 0.1 ml iBAC (2.78 M) were introduced into the reactor following which 0.25 ml 2-P was added after a 10-minute activation period. After the last sample had been taken (180 min.) a vacuum was drawn in the reactor during 10 minutes and the reactor was heated slightly for removal of 2-B, 2-P and 3-H. Subsequently, 0.25 ml 2-P was again added, without previous activation with iBAC. This procedure was then repeated. The conversion measured as a function of the time of the three successive metathesis reactions is presented in Table 3.

TABLE 3

Conversion of 2-P as a function of time and the amount of 2-P when using $SiO_2/WCl_4(O-2.6-C_6H_3(t-Bu)_2)_2/iBAC$ as catalyst

| Time (min) | 1st time 0.25 ml 2-P | 2nd time 0.25 ml 2-P | 3rd time 0.25 ml 2-P |
| --- | --- | --- | --- |
| 5 | 30 | 16 | 2 |
| 10 | 48 | 29 | 6 |
| 20 | 56 | 39 | 9 |
| 40 | 70 | 43 | 10 |
| 60 | 71 | 47 | 10 |
| 120 | 72 | 53 | 10 |
| 180 | 71 | 53 | 10 |

Example II

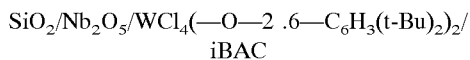
$SiO_2/Nb_2O_5/WCl_4(-O-2.6-C_6H_3(t-Bu)_2)_2/$ iBAC

A solution of 2,6-di-t-butylphenol (HO—2,6—$C_6H_3$(t-Bu)$_2$) (0.0420 g; $2.0375.10^{-4}$ mol) in n-hexane was added dropwise in a period of 5 minutes to 0.0404 g ($1.0187.10^{-4}$) $WCl_6$ in 30 ml hexane, after which the reaction mixture was refluxed for 2 hours. During Cl substitution by the phenoxide, the colour of the solution changed into dark purple. 0.52 g Of the modified support ($SiO_2/Nb_2O_5$) was heated under vacuum for 2 hours at 200° C. Then the hexane solution of $WCl_4(-O-2.6-C_6H_3(t-Bu_2)_2)$ was added, after which the reaction mixture was refluxed for 2 hours. The modified support turned brown, while the solution lost its colour. After settling of the reaction product the supernatant liquid was removed and the reaction product was subsequently washed 3 times with n-hexane and dried at 120° C. under vacuum. The catalyst contained 3.6% tungsten.

Measurement Of The Conversion 50 mg Of the dried $SiO_2/Nb_2O_5/WCl_4(-O-2.6-C_6H_3(t-Bu_2)_2)$ catalyst was transferred to the reactor vessel in an argon atmosphere. 4.4 ml PhCl and 0.1 ml iBAC (2.78 M) were added, and after a 10-minute activation period 0.5 ml 2-P was added. The reaction was carried out at room temperature. After the equilibrium had been attained, the solution was removed under vacuum. The equilibrium was considered to have been reached when the conversion no longer increased significantly with time. Again, 4.5 ml PhCl and 0.5 ml 2-P were added to the dry catalyst, without previous activation with iBAC, after which the metathesis activity was measured again. This was repeated four times. The conversion measured as a function of the time of the 5 successive metathesis reactions is presented in Table 4.

TABLE 4

Conversion of 2-P as a function of time when using $SiO_2/Nb_2O_5/WCl_4(O-2.6-C_6H_3(t-Bu_2)_2/iBAC$ as catalyst

| 2-P additions (0.5 ml) | Time (min.) | % conversion |
| --- | --- | --- |
| 1 time | 5 | 55 |
|  | 20 | 70 |
| 2 times | 5 | 63 |
|  | 20 | 69 |
| 3 times | 5 | 55 |
|  | 20 | 64 |
| 4 times | 5 | 62 |
|  | 20 | 68 |
|  | 90 | 78 |
| 5 times | 5 | 57 |
|  | 30 | 60 |

From the results of Example II it appears that the catalyst according to the invention has a higher initial conversion, even at double the amount of substrate and half the amount of catalyst, than the catalyst from comparative experiment B. It is further found that the activity has not decreased significantly after 5 successive additions of 0.5 ml 2-P, while the activity of the catalyst of comparative experiment B has all but disappeared after 2 additions of 0.25 ml 2-P. From Basset, J. Mol. Cat., 76 (1992), 287–295, it can be calculated that 2.5 mol of 2-B per minute is formed per mol of catalytic metal in metathesis of 2-P using an $Nb_2O_5/CH_3ReO_3$ catalyst. From Example II it can be calculated that when the catalyst according to the invention is used 3.63 mol of 2-B is formed per minute per mol of catalytic metal (calculation: 5 times 4.63 mmol 2-B per $9.79.10^{-3}$ mmol tungsten in 165 minutes). Thus, the activity of the catalyst according to the invention is significantly higher.

Comparative Experiment C: $SiO_2/WO_3$

A catalyst was prepared by impregnation of silica with an aqueous solution of $NH_4WO_4$ followed by drying and calcination at 600° C.

Measurement Of The Conversion 100 mg Of this catalyst was transferred to the reactor and vacuum-dried for 2 hours at 110–120° C. for removal of the physically adsorbed water. In an argon atmosphere 10 ml PhCl and 0.2 ml (2.83 M) iBAC were added following which, after a 10-minute activation period, 0.25 ml 2-P was added. The reaction was carried out at room temperature. The conversion measured as a function of time is presented in Table 5.

TABLE 5

Conversion of 2-P as a function of time when using $SiO_2/WO_3/iBAC$ as catalyst

| Time (min.) | % conversion |
| --- | --- |
| 5 | 14 |
| 10 | 25 |
| 20 | 36 |
| 40 | 53 |
| 60 | 59 |

Example III: $SiO_2/Nb_2O_5/WO_3/iBAC$

The catalyst prepared in Example I was oxidized at 400° C. A catalyst was obtained in which the tungsten has been oxidized to $WO_3$.

Measurement Of The Conversion 10 ml PhCl and 0.1 ml iBAC (2.78 M) were added to 50 mg of this catalyst, following which, after a 10-minute activation period, 0.5 ml 2-P was added. The reaction was carried out at room temperature. The conversion measured as a function of time is presented in Table 6.

TABLE 6

Conversion of 2-P as a function of time when using SiO$_2$/Nb$_2$O$_5$/WO$_3$/iBAC as catalyst

| Time (min.) | Conversion (%) |
|---|---|
| 5 | 12 |
| 15 | 27 |
| 120 | 56 |
| 160 | 69 |

From Example III it appears that with double the amount of substrate and half the amount of catalyst the catalyst according to the invention has a conversion that is comparable to that of the catalyst of comparative experiment C. As a consequence, the activity of the catalyst is about 4 times as high.

We claim:

1. A heterogeneous metathesis catalyst comprising a support;
   a first layer, wherein said first layer is a promoter, said promoter wholly or partially covering said support to thereby form a modified support, said promoter comprising a niobium compound; and
   a second layer, wherein said second layer is a metal compound wholly or partially covering said modified support, wherein said metal compound has been attached to the modified support by oxygen bridges, the metal compound being of the formula:

$M(X)_n(R)_m(O)_p$ wherein:
   M represents tungsten, rhenium or molybdenum;
   X represents halogen or —OH;
   R represents organic groups, different or the same, selected from the group consisting of alkyl, aryl, alkoxy, aryloxy, carbonyl, alkylidene and π-bonded hydrocarbons, containing 1–25 carbon atoms;
   O represents an oxygen bridge to the support;
   n+m+p=5, 6 or 7; and
   p=1, 2 or 3.

2. The catalyst of claim 1, wherein the niobium compound is a niobic acid monolayer.

3. The catalyst of claim 1 or 2, wherein the support consists substantially of silica.

4. The catalyst of claim 1 or 2, wherein the metal is tungsten.

5. The catalyst of claim 1, wherein the metal complex contains one to four substituted or non-substituted aryloxy groups.

6. Catalyst of claim 1 wherein R contains 12 or more carbon atoms.

7. Catalyst according to claim 1 wherein R is a bidentate ligand.

8. A process for the preparation of a catalyst according to claim 1, said process comprising the following steps:
   (a) reacting, in a solvent and in the absence of water and oxygen, a support with a niobium compound;
   (b) treating the reaction product obtained in (a) with a solution of an ammonium salt or ammonium hydroxide;
   (c) heating the reaction product obtained in (b) at a temperature between 100 and 300° C. at reduced pressure;
   (d) moistening the reaction product obtained in (c) with water;
   (e) heating the reaction product obtained in (d) at a temperature between 100 and 300° C. at reduced pressure; and
   (f) attaching the metal compound to the modified support obtained in (e) via chem absorption of a metal compound on that modified support.

9. A process for the preparation of a catalyst of claim 8, characterized in that the niobium compound is Nb(O—R$^1$)$_5$ with R$^1$ being alkyl, aryl, alkaryl, aralkyl or mixtures of these groups, R$^1$ containing 1–20 carbon atoms.

10. A process for the preparation of a catalyst according to claim 8 or claim 9, characterized in that the metal compound is of the formula:

$M(X)_n(R)_{p-n}$, where:
    M : W, Re, Mo
    X : halogen
    R : compounds, different or the same, chosen from the group consisting of alkyl, aryl, alkoxy, aryloxy, carbonyl, alkylidene or π-bonded hydrocarbons, containing 1–25 carbon atoms n=1 to (p-1), p=5, 6 or 7.

11. A process for activating a catalyst of claim 8, wherein the catalyst is reacted with any alkylating organometallic compound.

12. Process comprising using a catalyst according to claim 1, or as obtainable through the process according to claim 8 to metathesize olefins.

13. Process for the metathesis of olefins of claim 12, wherein the process is carried out at a temperature between 0 and 30° C.

14. The process of claim 11, wherein the alkyl organometallic compound is an aluminum alkyl compound.

15. The process of claim 14, wherein the aluminum alkyl compound is an isobutyl aluminum dihalide.

* * * * *